United States Patent [19]

Warren

[11] Plant 4,704

[45] Apr. 28, 1981

[54] BLUEGRASS

[75] Inventor: Benedict O. Warren, Palos Hills, Ill.

[73] Assignee: Warren's Turf Nursery, Inc., Palos Hills, Ill.

[21] Appl. No.: 70,275

[22] Filed: Aug. 27, 1979

[51] Int. Cl.[3] ..... A01H 5/00

[52] U.S. Cl. ..... Plt./88

[58] Field of Search ..... Plt./88

*Primary Examiner*—Robert E. Bagwill
*Assistant Examiner*—James R. Feyrer
*Attorney, Agent, or Firm*—Townsend and Townsend

[57] ABSTRACT

A new and distinct variety of Kentucky Bluegrass (*Poa pratensis* L.) characterized by its excellent tolerance to drought, low fertilizer requirements, deep rooting system, excellent tolerance to Fusarium blight, and good to excellent shade tolerance. The plant tolerates a close cut, is highly resistant to most common bluegrass diseases, is extremely aggressive, has a medium to course leaf texture and consistently maintains excellent turf quality.

5 Drawing Figures

WTN-H7 Kentucky bluegrass is a perennial with a softness in its leaves that makes it attractive and rich in color even under mowing heights of 1.3 cm. It is a turf type with a tiller density of 1500+ tillers/square foot. Of special importance is its ability to withstand diseases such as Helminthsporium leafspot and fusarium blight. Its deep rooting rhizomes and roots give it excellent regrowth potential or excellent capacity to regenerate itself via its root system. The new invention can maintain good turf quality under 65% shade and it maintains excellent turf quality under full sunlight.

The WTN-H7 is important because of its distinctness in having superior qualities over a broad spectrum. It will become apparent as more detailed information is given in conjunction with the following illustrations in which.

Figure 1:
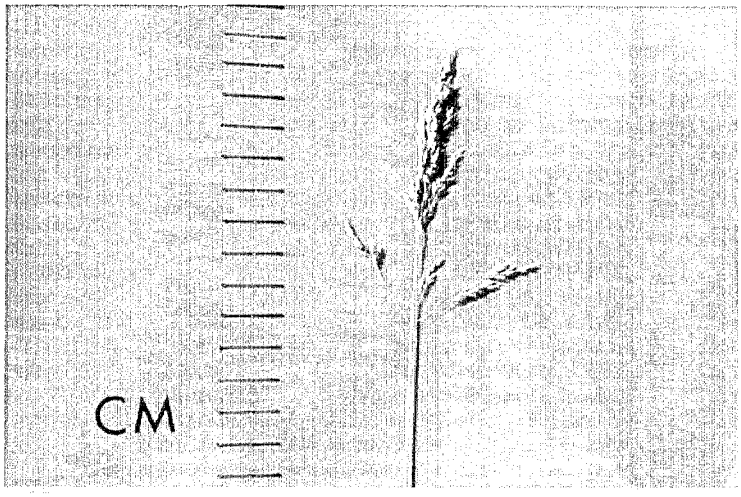
FIG. 1 shows a panicle of the new variety two weeks after the onset of flowering.
Figure 2:
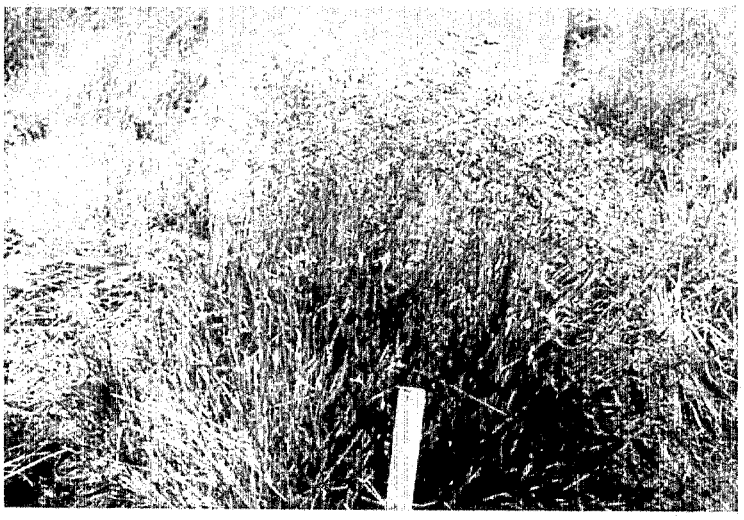
FIG. 2 shows a plant after the completion of flowering.
Figure 3:
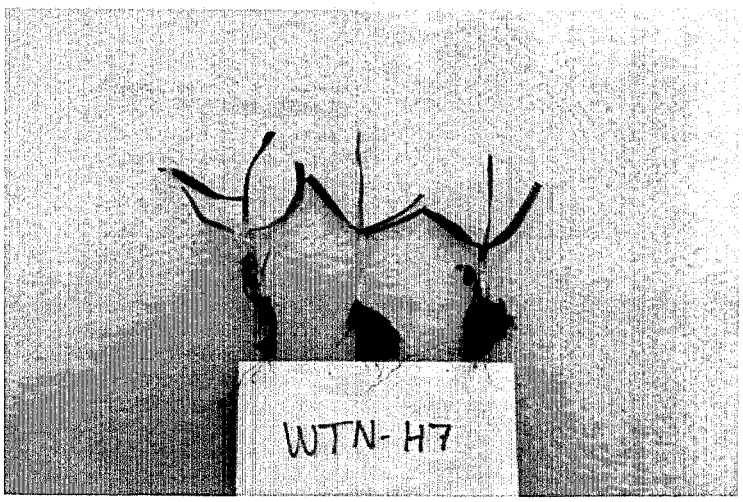
FIG. 3 shows some typical tillers of WTN-H7 extracted from a closely mowed turf.
Figure 4:
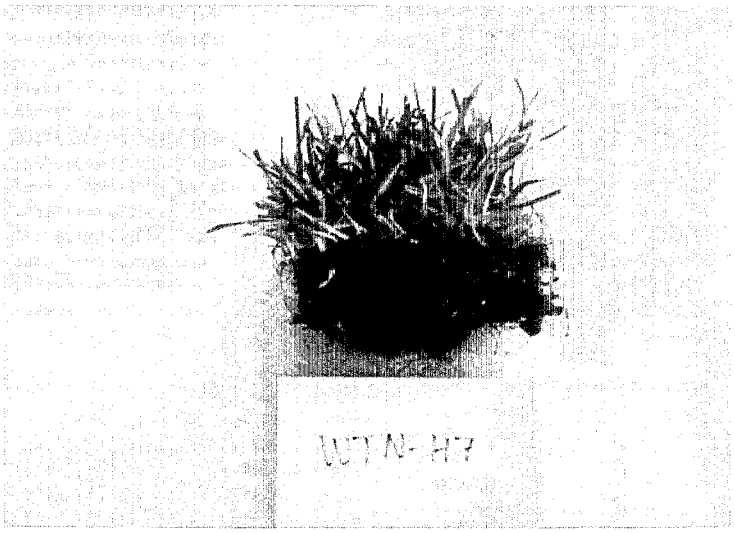
FIG. 4 shows some turf of the new invention at a cutting height of 2.5 cm.
Figure 5:
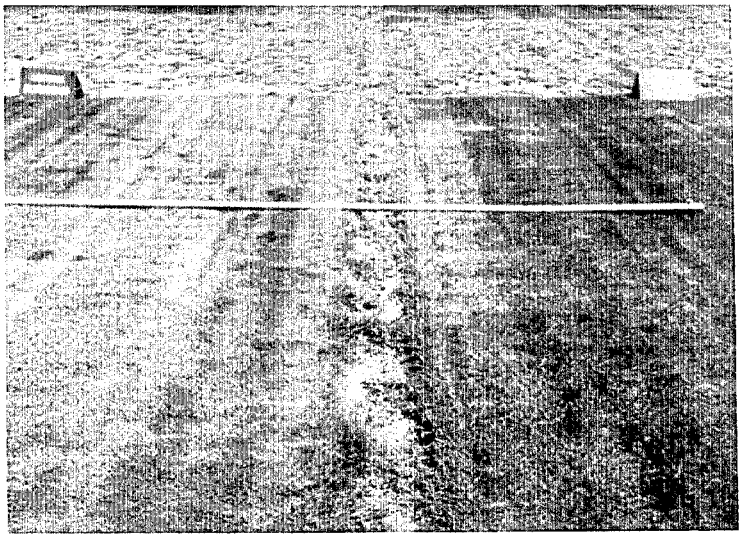
FIG. 5 shows the relative drought tolerance of the WTN-H7 as compared with Merion Kentucky bluegrass.

The WTN-H7 exhibits its uniqueness in the following ways:

(1) Excellent drought tolerance;

(2) Excellent shade tolerance as compared to other bluegrasses;

(3) Heavy seed panicles;

(4) Very good turf density;

(5) Excellent turf quality;

(6) A medium green color;

(7) A distinctive purpling of the panicle of flowering;

(8) A medium to coarse leaf texture;

(9) Excellent resistance to fusarium blight and Helminthsporium leaf spot;

(10) Highly apomictic (90-98%).

The color references herein are to *Royal Horticultural Society Color Chart* (1941), by Robert F. Wilson. The readings were taken on July 24, 1979 on mature tillers using the first leaf on each tiller on heavily watered, fertilized turf, at Suisun City, Calif.

Plant description: Under conditions such as those experienced in the summer of 1976 at Palos Hills, Ill. and in the summer of 1978 at Hubbard, Oreg., the following plant description of WTN-H7 can be made based on average measurements.

When allowed to flower, the culms of the new invention are moderately bending at the upper nodes and are tufted, moderately stout, smooth, glossy, and cylindrical with 4 to 5 nodes—the lower three being very close together. The plant reaches a height of 77.8 cm. with an average panicle length of 11.2 cm., a flag leaf width of 4.8 mm. The leaves are medium to light medium green in color (137 C Green Group) and the sheaths are smooth and hairless with a ligule length of 6 mm. The panicles are pyramidal and semi-open with the main axis erect until seed set at which time it droops heavily to one side. The panicles are purplish during flowering; averaging 3.5 branches at the lower end of the panicle. The average length of the spikelet is 4.2 mm. with approximately 4.9 florets/spikelet. The spikelets are ovate and compressed with the upper spikelets in clusters with close branching and the lower branching wider spaced; the glumes are unequal with the upper ovate measuring 2.0 mm. Lemmas are overlapping, oblong to ovate, averaging 2.8 mm. in length. There are fine hairs at the base and the lower half of the lemmas. The paleas are 2.3 mm. in length. The caryopses are tightly enclosed by a lemma and palea.

Under mowing (3.2 cm.) the number of tillers/square inch average out to 20 with 3.5 leaves/plant at an average leaf width (2d leaf) of 2.7 mm. The ligules are very short and the leaf is light to medium green in color with a keel shape and a boat shaped tip. The chromosome count is approximately $2n=42$ and the apomixis level is about 95%.

The measurements as explained were made under conditions of the weather in 1976 and 1978 at two different locations. These measurements will vary to a certain degree as conditions under which the grass is grown will vary. Morphological comparisons of WTN-H7 and other Kentucky bluegrasses are listed in Table one.

TABLE ONE

Morphological Comparisons of the New Invention and Other Bluegrasses Taken During Flowering at Hubbard, Oregon, in 1978.

| Variety | Plant Height (cm.) | Panicle Length (cm.) | Flag Leaf Length (cm.) | Flag Leaf Width (mm.) |
|---|---|---|---|---|
| WTN-H7 | 77.8 | 11.2 | 10.3 | 4.8 |
| WTN-H6 | 66.1 | 12.6 | 9.1 | 4.9 |
| WTN-I13 | 65.5 | 13.6 | 10.4 | 4.0 |
| Baron | 60.0 | 7.9 | 4.3 | 2.5 |
| Adelphi | 69.9 | 9.6 | 3.9 | 2.5 |

Turf characteristics: The new variety had consistently exhibited excellent turf quality in plots located across the country. Overall turf quality ratings are indicated in tables Two, Three, Four, Five, Six and Nine. As well, the grass has been in other trials which indicate its ability to withstand many environmental changes. Personal observation and correspondence with other researchers have indicated that the new invention can withstand cold weather as well as wet and damp weather, and hot and dry weather such as that of Suisun City, Calif.

TABLE TWO

Relative Comparisons for WTN-H7 and Other Bluegrasses for Turf Quality, Color, Density, and Drought Tolerance Taken in 1978 on Replicated Plots Established in 1975 at Anderson, Indiana.

| Variety | Turf[1] Quality | Density[2] | Color[3] | Drought[4] Tolerance |
|---|---|---|---|---|
| WTN-H7 | 6.1 | 4.3 | 4.7 | 4.3 |
| Glade | 4.0 | 3.0 | 2.0 | 2.5 |
| Adelphi | 4.3 | 3.5 | 3.3 | 3.7 |
| Brunswick | 4.6 | 3.0 | 2.3 | 2.7 |
| Baron | 4.0 | 2.7 | 2.7 | 2.7 |
| Touchdown | 3.9 | 2.7 | 2.0 | 1.7 |

[1]Scale: 1 = worst; 9 = best; based on six observations.
[2]Scale: 1 = worst; 5 = best; based on three observations.
[3]Scale: 1 = worst; 5 = best; based on three observations (drought tolerance was a factor).
[4]Scale: 1 = worst; 5 = best; based on three observations (three weeks of temperatures in the 90's preceded these readings).

TABLE THREE

Relative Comparisons for Turf Quality Taken on Replicated Trials Established Vegetatively in June of 1975 at Palos Hills, Illinois.

| Variety | 1976* | 1977* | 1978* |
|---|---|---|---|
| WTN-H7 | 5.0 | 5.3 | 6.9 |
| Touchdown | 4.0 | 4.0 | 5.2 |
| Glade | 4.7 | 4.0 | 4.1 |
| Adelphi | 4.8 | 4.0 | 4.7 |
| Baron | 4.3 | 4.3 | 4.7 |
| Merion | 4.0 | 5.3 | 4.3 |

*Scale: 1 = worst; 9 = best

TABLE FOUR

Relative Comparisons for Turf Performance, Stem Rust, and Dollar Spot Tolerance on WTN-H7 and Other Bluegrasses Taken in 1976 at Adelphia, New Jersey, on Plots Established in 1974 by Rutgers University.[1 5]

| Variety | Rust[2] | Dollar Spot[3] Mean | Turf[4] Performance |
|---|---|---|---|
| WTN-H7 | 1.0 | 31 | 6.5 |
| A34 | 1.5 | 56 | 6.0 |
| Nugget | 2.5 | 231 | 5.6 |
| Victa | 1.9 | 48 | 6.4 |
| Merion | 7.5 | 43 | 5.5 |
| Baron | 2.5 | 75 | 5.9 |

TABLE FOUR-continued

Relative Comparisons for Turf Performance, Stem Rust, and Dollar Spot Tolerance on WTN-H7 and Other Bluegrasses Taken in 1976 at Adelphia, New Jersey, on Plots Established in 1974 by Rutgers University.[1 5]

| Variety | Rust[2] | Dollar Spot[3] Mean | Turf[4] Performance |
|---|---|---|---|
| Touchdown | 6.3 | 101 | 6.3 |

[1]Turf Plots for the WTN-H7 were in the same area as the commercial grasses.
[2]Scale: 1 = best.
[3]Average number of spots.
[4]Turf Performance: 9 = best.
[5]Information is from Rutgers University.

One of the strongest points of this new invention which separates it from other varieties and makes it distinct is its shade tolerance. Kentucky bluegrasses in general do very poorly under shade conditions of 65% or more. At the present time there are only a few Kentucky bluegrasses which are considered shade grasses. WTN-H7 has been consistently ranked at or near the top for shade tolerance in trials in Chicago and in Ohio as indicated in Tables Five and Six.

TABLE FIVE

Relative Comparisons of Shade Tolerance for WTN-H7 and Other Bluegrasses Taken in 1976, 1977 and Overall Average for 1976, 1977, and 1978 at Columbus, Ohio, on Plots Established in 1975.[1]

| Variety | Turf*(76) Quality | Turf*(77) Quality | Overall *(76, 77, & 78) |
|---|---|---|---|
| WTN-H7 | 5.2 | 5.3 | 5.8 |
| Nugget | 5.0 | 4.3 | 5.2 |
| Glade | 4.9 | 5.0 | 4.4 |
| A34 | 4.4 | 4.3 | 4.4 |
| Victa | 3.1 | 2.0 | 2.8 |
| Merion | 3.0 | 3.3 | 2.9 |
| Bristol | 5.5 | 4.5 | 5.1 |

*Scale: 1 = worst; 9 = best.
[1]Information from Ohio State University, Columbus, Ohio.

TABLE SIX

Relative Comparison of Shade Tolerance for WTN-H7 and Other Bluegrasses Taken in 1975 and 1976 at Palos Hills, Illinois, is in Replicated Trials Under 65% Shade.

| Variety | 1975* | 1976* |
|---|---|---|
| WTN-H7 | 6.8 | 5.8 |
| Nugget | 4.9 | 4.0 |
| Glade | 5.3 | 5.8 |
| A34 | 5.6 | 5.0 |

*Scale: 9 = best.

Tolerance to dry conditions is another strong point of the new invention. WTN-H7 has had the ability to withstand drought conditions for a longer period of time than most other Kentucky bluegrasses. Table Two presents some data taken at Anderson, Ind. after a long dry period. Observations of areas where WTN-H7 is planted indicate a lower water requirement for its survival.

Disease tolerance: A comparison of WTN-H7 and other bluegrasses for resistance or tolerance to stem rust incited by *Puccinia graminis,* dollar spot incited by *Sclerotinia homoecarpa,* leaf spot incited by *Drechslera poae,* Fusarium blight incited by Fusarium sp., and powdery mildew as incited by *Erysiphe graminis* are given in tables Four, Seven, Eight and Nine. Stripe and flag smut caused by *Ustilago striiformis* and *Ustilago agropyrina* respectively have been in experimental varieties of bluegrasses surrounding the new invention, but thus far, the WTN-H7 has remained free of it.

TABLE SEVEN

Relative Comparisons for Leaf Spot Resistance Taken on Replicated Plots that were Established in 1971 at Palos Hills, Illinois.

| Variety | % Leaf spot*(74) | % Leaf Spot*(76) |
|---|---|---|
| WTN-H7 | 3.5 | 1.7 |
| A34 | 10.5 | 7.7 |
| A20 | 4.3 | 1.3 |
| Merion | 6.2 | 3.0 |
| Common | 41.7 | 15.0 |
| I33 | 11.3 | 10.0 |

*Expressed as % of plot affected by the spotting and % of the plant affected.

TABLE EIGHT

Relative Comparisons of Mildew Resistance for WTN-H7 and Other Bluegrasses Taken in 1976 and 1977 at Columbus, Ohio, on Plots Established in 1975.[1]

| Variety | 1976* | 1977* |
|---|---|---|
| WTN-H7 | 2.3** | 1.6** |
| Nugget | 2.0** | 2.0** |
| Glade | 1.7** | 1.3** |
| Victa | 9.0 | 9.0 |
| Merion | 8.7 | 9.0 |

*Scale: 1 = most tolerant.

**Not significantly different.

[1]Information from Ohio State University, Columbus, Ohio.

TABLE NINE

Relative Comparisons for Fusarium Blight Resistance Taken at the Danville Country Club, Danville, Illinois, in 1975 on plots that were Established in 1974 by Use of 8 inch plugs. Relative Agressiveness of the grasses expressed as percent cover are given as well for 1975 and 1978. Percent cover is based on a base level of 100% or the original size of each plot.

| Variety | Fusarium*(75) | % Cover (75) | % Cover (78) |
|---|---|---|---|
| WTN-H7 | 1.3 | 116 | 133 |
| A20 | 2.2 | 87 | 106 |
| Baron | 2.5 | 41 | 82 |
| Fylking | 6.8 | 70 | 82 |

*Scale: 1 = best.

Based on three replications.

Propagation and reproduction: In addition to its above listed qualities, the new variety has the ability to reproduce itself by seed maintaining its integrity as a result of being 90–99% apomictic. It has a very deep root and rhizome system lending itself to excellent regrow potential and excellent healing. Its agressiveness is indicated by date in Table Nine.

The new invention responds well to fertilizer but is not in need of large quantities to maintain good turf quality. Plots have been maintained at both 2 pounds of Nitrogen/year and 8 pounds of nitrogen/year without the grass being noticeably affected. It had good turf quality at the low rate and excellent turf quality at the high rate without having any noticeable increase in disease activity.

I claim:

1. The new and distinct variety of Bluegrass Plant herein described and illustrated and identified by the characteristics enumerated above.

* * * * *